United States Patent [19]
Richter et al.

[11] 4,001,179
[45] Jan. 4, 1977

[54] BIS-(TETRAHALOPHTHALIMIDOCAR-BONYL)-BENZENE
[75] Inventors: Sidney B. Richter, Chicago; Glendon D. Kyker, Glen Ellyn, both of Ill.
[73] Assignee: Velsicol Chemical Corporation, Chicago, Ill.
[22] Filed: Mar. 21, 1975
[21] Appl. No.: 560,453
[52] U.S. Cl. .................. 260/45.75 B; 252/8.1; 260/22 R; 260/45.75 V; 260/45.75 W; 260/326 N; 260/800
[51] Int. Cl.² .................. C07D 209/48; C08K 5/00
[58] Field of Search ... 260/326 N, 45.8 N, 45.75 B, 260/45.75 V, 45.75 W
[56] References Cited
UNITED STATES PATENTS
2,558,675  6/1951  Flory ........................... 260/326 N
3,868,388  2/1975  Dotson, Jr. et al. .......... 260/45.8 N OTHER PUBLICATIONS
Sonnenberg, "Chem. Abstracts," vol. 74, p. 57, No. 126,845a (1971).
Subject Index (1967–1971), p. 24173s.

Primary Examiner—Lewis Gotts
Assistant Examiner—S. P. Williams
Attorney, Agent, or Firm—Robert J. Schwarz; Dietmar H. Olesch

[57] ABSTRACT

This invention discloses chemical compounds of the formula

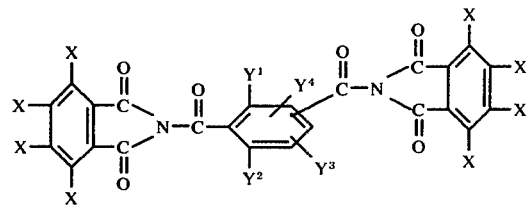

wherein X is chlorine or bromine and each of $Y^1$, $Y^2$, $Y^3$ and $Y^4$ are hydrogen, chlorine or bromine. Further disclosed are combustible polymers which have incorporated therein a fire retardant amount of a compound of the foregoing description.

13 Claims, No Drawings

BIS-(TETRAHALOPHTHALIMIDOCARBONYL)-BENZENE

This invention relates to new compositions of matter and more specifically relates to new chemical compounds of the formula (I)

wherein X is chlorine or bromine and each of $Y^1$, $Y^2$, $Y^3$ and $Y^4$ are hydrogen, chlorine or bromine.

The compounds of the present invention possess exceptional properties in rendering combustible polymers fire retardant when intimately admixed therewith.

The compounds of the present invention can be conveniently prepared by reacting an isophthaloyl dichloride or terephthaloyl dichloride of the formula (II)

wherein $Y^1$, $Y^2$, $Y^3$ and $Y^4$ are as heretofore described, with two molar amounts of a tetrahalophthalimide of the formula (III)

wherein X is as heretofore described. This reaction can be effected by combining the compounds of formulae II and III in an inert organic reaction medium in the presence of an acid acceptor such as a tertiary amine. The reaction mixture can then be heated at reflux for a period of from about 1 to about 24 hours to ensure completion of the reaction. After this time the mixture can be filtered and the filtrate can be stripped of solvent to yield the desired product. This product can be used as such or can be further purified by conventional techniques such as washing, recrystallizing and the like.

Exemplary suitable phthaloyl dichlorides useful for preparing the compounds of the present invention are isophthaloyl dichloride, 5-chloroisophthaloyl dichloride, 5-bromoisophthaloyl dichloride, 4,5-dichloroisophthaloyl dichloride, 4,5-dibromoisophthaloyl dichloride, 2,4,5-tri-chloroisophthaloyl dichloride, 2,4,5,6-tetrachloroisophthaloyl dichloride, 2-chloroterephthaloyl dichloride, 2-bromoterephthaloyl dichloride, 2,6-dichloroterephthaloyl dichloride, 2,6-dibromoterephthaloyl dichloride, 2,3,5,6-tetrachloroterephthaloyl dichloride, 2,3,5,6-tetrabromoterephthaloyl dichloride, terephthaloyl dichloride and the like.

The phthalimides of formula II useful for preparing the compound of this invention are tetrachlorophthalimide and tetrabromophthalimide.

The manner in which the compounds of this invention can be prepared is more specifically illustrated in the following examples.

EXAMPLE 1

Preparation of 1,4-Bis-(3,4,5,6-Tetrachlorophthalimidocarbonyl)benzene 3,4,5,6-Tetrachlorophthalimide (0.04 mole), benzene (500 ml) and triethylamine (0.045 mole) are charged into a glass reaction vessel equipped with a mechanical stirrer, thermometer and reflux condenser. Terephthaloyl dichloride (0.02 mole) is added dropwise with stirring to the reaction mixture at room temperature. After the addition is completed the reaction mixture is heated at reflux for a period of about 2 hours. After this time the mixture is filtered and the filtrate is washed with water. The washed solution is then dried over anhydrous magnesium sulfate, filtered and stripped of solvent to yield the desired product 1,4-bis-(3,4,5,6-tetrachlorophthalimidocarbonyl)benzene.

EXAMPLE 2

Preparation of 1,3-Bis-(3,4,5,6Tetrabromophthalimidocarbonyl)benzene 3,4,5,6-Tetrabromophthalimide (0.04 mole), benzene (500 ml) and pyridine (0.045 mole) are charged into a glass reaction vessel equipped with a mechanical stirrer, thermometer and reflux condenser. Isophthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,3-bis-(3,4,5,6-tetrabromophthalimidocarbonyl)-benzene.

EXAMPLE 3

Preparation of 1,4-Bis-(3,4,5,6-Tetrachlorophthalimidocarbonyl)-2,6-Dichlorobenzene 3,4,5,6-Tetrachlorophthalimide (0.04 mole), benzene (500 ml) and pyridine (0.045 mole) are charged into a glass reaction vessel equipped with a mechanical stirrer, thermometer and reflux condenser. 2,6-Dichloroterephthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,3-bis-(3,4,5,6-tetrachlorophthalimidocarbonyl)-2,6-dichlorobenzene.

EXAMPLE 4

Preparation of
1,4-Bis-(3,4,5,6-Tetrabromophthalimidocarbonyl)-2,3,5,6-Tetrachlorobenzene 3,4,5,6-Tetrabromophthalimide (0.04 mole), benzene (500 ml) and pyridine (0.045 mole) are charged into a glass reaction vessel equipped with a mechanical stirrer, thermometer and reflux condenser. 2,3,5,6-Tetrachloroterephthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,4-bis-(3,4,5,6-tetrabromophthalimidocarbonyl)-2,3,5,6-tetrachlorobenzene.

EXAMPLE 5

Preparation of
1,4-Bis-(3,4,5,6-Tetrachlorophthalimidocarbonyl)-2,3,5,6-tetrabromobenzene 3,4,5,6-Tetrachlorophthalimide (0.04 mole), benzene (500 ml) and pyridine (0.045 mole) are charged into a glass reaction vessel equipped with a mechanical stirrer, thermometer and reflux condenser. 2,3,5,6-Tetrabromoterephthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,4-bis-(3,4,5,6-tetrachlorophthalimidocarbonyl)-2,3,5,6-tetrabromobenzene.

EXAMPLE 6

Preparation of
1,3-Bis-(3,4,5,6-Tetrabromophthalimidocarbonyl-4-bromobenzene 3,4,5,6-Tetrabromophthalimide (0.04 mole), benzene (500 ml) and pyridine (0.045 mole) are charged into a glass reaction vessel equipped with a mechanical stirrer, thermometer and reflux condenser. 4-Bromoisophthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,3-bis-(3,4,5,6-tetrabromophthalimidocarbonyl-4-bromobenzene.

EXAMPLE 7

Preparation of
1,3-Bis-(3,4,5,6-Tetrabromophthalimidocarbonyl)-2,6-dichlorobenzene 3,4,5,6-Tetrabromophthalimide (0.04 mole), benzene (500 ml) and pyridine (0.045 mole) are charged into a glass reaction vessel equipped with a mechanical stirrer, thermometer and reflux condenser. 2,6-Dichloroisophthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,3-bis-(3,4,5,6-tetrabromophthalimidocarbonyl)-2,6-dichlorobenzene.

EXAMPLE 8

Preparation of
1,4-Bis-(3,4,5,6-Tetrabromophthalimidocarbonyl)benzene 3,4,5,6-Tetrabromophthalimide (0.04 mole), benzene (500 ml) and pyridine (0.045 mole) are charged into a glass reaction vessel equipped with a mechanical stirrer, thermometer and reflux condenser. Terephthaloyl dichloride (0.02 mole) is added dropwise with stirring to the reaction mixture at room temperature. After the addition is completed the reaction mixture is heated at reflux for a period of about 2 hours. After this time the reaction mixture is filtered and the filtrate is washed with water. The washed solution is then dried over anhydrous magnesium sulfate, is filtered and stripped of solvent under reduced pressure to yield the desired product 1,4-bis-(3,4,5,6-tetrabromophthalimidocarbonyl)benzene.

organic polymeric compositions find wide application in the manufacture of molded and extruded articles as well as in paints, films, coatings and miscellaneous products. Since the great majority of organic polymeric compositions are highly flammable it is desirable to render these fire retardant. It has been found that the compound of this invention possesses the desirable property of rendering organic polymers fire retardant when incorporated therein.

Thus, a further embodiment of the present invention resides in fire retardant polymeric compositions comprising a combustible polymer and a fire retardant amount of a compound of this invention.

The compounds of this invention impart fire retardant properties to combustible polymers by forming intimate admixtures therewith. These admixtures can be readily prepared by one of several methods well known in the art. For example the compounds can be admixed into the combustible polymer while the latter is dissolved in a suitable solvent. This procedure is especially useful when it is desired to incorporate the compound during the preparation of the polymer. The compounds of this invention can also be mixed with a combustible polymer in the molten state at a temperature that can range from the melting point of the polymer to a temperature just below the decomposition temperature of the polymer. Another method of forming an intimate admixture comprises dry blending the compounds with the polymer in the finely divided state. Subsequent molding or extrusion of this blend can then result in a substantially homogeneous composition.

The fire retardant polymeric compositions of the instant invention can contain a fire retarding amount of one or more compounds of this invention. A fire retarding amount of a compound can range from about 5 to about 50 weight percent of the total composition. The exact amount of compound employed will depend upon such factors as the degree of fire retardancy desired, the specific combustible polymer used, the end use of the resulting product and the like.

The compounds of this invention can impart fire retardant properties to a variety of combustible polymers. Exemplary of such polymers which can be used in admixture with the compounds to form the fire retardant polymeric compositions of this invention are the homopolymers and copolymers of unsaturated aliphatic, cycloaliphatic, and aromatic hydrocarbons, such as polyethylene, polypropylene, polybutene, ethylene propylene copolymers, copolymers of ethylene or propylene with other olefins, polybutadiene, polymers of butadiene, polyisoprene, polystyrene, polyvinylidene, and polymers of pentene, hexene, heptene, octene 2-methylpropene-1, 3-methylbutene-1, 4-methylpentene-1, 4-methylhexene-1, 5-methylhexene-1, bicyclohexene (2.2.1), pentadiene, hexadiene, 2,3-dimethylbutadiene-1,3, 2-methylpentadiene, vinylcyclohexene such as 4-vinylcyclohexene, cyclopentadiene, methylstyrene and the like. Other useful polymers include indene-coumarone resins, polymers of acrylate esters and polymers of methacrylate esters, acrylate and methacrylate resins such as ethyl acrylate, n-butyl methacrylate, isobutyl methacrylate, ethyl methacrylate, and methyl methacrylate, alkyd resins, hydrocarbon resins from petroleum, isobutylene resins, polyurethanes, polyester resins such as unsaturated polyesters of dibasic acids and dihydroxy compounds, polyester elastomers, saturated thermoplastic polyesters, polyisobutylene, rubbers such as natural rubber, synthetic polyisoprene, polybutadiene, cyclized rubber, butadiene-acrylonitrile rubber, butadiene-styrene rubber, butyl rubber, neoprene rubber, terpene resins, urea resins, vinyl resins such as poly(vinyl acetal), poly(vinyl acetate), vinyl alcohol-acetate copolymer, poly(vinyl alcohol), poly(vinyl alkyl ether), vinyl methyl ether-maleic anhydride copolymer, poly(vinyl butyral), vinyl chloride-acetate copolymer, poly(vinyl pyrrolidone), vinylidene chloride copolymers and the like. Additional useful polymers include nylon, diallyl phthalates and phthalate resins and polycarbonates.

The fire retardant compositions of this invention can also contain adjuvants which in conjunction with the compounds of this invention improve the fire retardancy of the composition and in some instances provide synergistic results not obtainable with the use of a compound alone. Such adjuvants can comprise antimony compounds such as antimony trioxide, zinc borate, lead arsenates such as PbHAsO$_4$ and the like. These adjuvants can comprise from about 1 to about 35% by weight of the total composition.

The effectiveness of the compounds of this invention as flame retardants can be demonstrated in an experiment wherein fire retardant compositions comprising a compound of the present invention and various combustible polymers are subjected to a flammability test using the oxygen index method. The flammability test is carried out in an accordance with the general procedures detailed in the ASTM D 2863-70 test method. This method provides a procedure for determining the relative flammability of plastics by measuring the minimum concentration of oxygen expressed as volume percent, in a slowly rising mixture of oxygen and nitrogen that will just support combustion.

We claim:

1. A compound of the formula

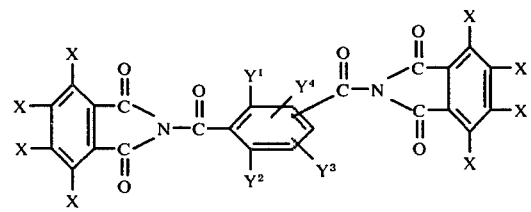

wherein X is chlorine or bromine and each of $Y^1$, $Y^2$, $Y^3$ and $Y^4$ are hydrogen, chlorine or bromine.

2. The compound of claim 1, 1,4-bis-(3,4,5,6-tetrachlorophthalimidocarbonyl)benzene.

3. The compound of claim 1, 1,3-bis-(3,4,5,6-tetrabromophthalimidocarbonyl)benzene.

4. The compound of claim 1, 1,4-bis-(3,4,5,6-tetrachlorophthalimidocarbonyl)-2,6-dichlorobenzene.

5. The compound of claim 1, 1,4-bis-(3,4,5,6-tetrabromophthalimidocarbonyl)-2,3,5,6-tetrachlorobenzene.

6. The compound of claim 1, 1,4-bis-(3,4,5,6-tetrachlorophthalimidocarbonyl)-2,3,5,6-tetrabromobenzene.

7. A fire retardant polymeric composition comprising a combustible polymer and a fire retarding amount of a compound of claim 1.

8. The composition of claim 7 wherein the combustible polymer is polystyrene.

9. The composition of claim 7 wherein the combustible polymer is polyethylene.

10. The composition of claim 7 wherein the combustible polymer is a terepolymer of acrylonitrile, butadiene and styrene.

11. The composition of claim 7 wherein the combustible polymer is polypropylene.

12. The composition of claim 7 wherein the combustible polymer is a polyester.

13. The composition of claim 7 which contains from about 1 to about 35% by weight of an adjuvant selected from the group consisting of antimony trioxide, zinc borate and lead arsenate.

* * * * *